United States Patent
Khalil et al.

(10) Patent No.: US 6,662,031 B1
(45) Date of Patent: Dec. 9, 2003

(54) METHOD AND DEVICE FOR THE NONINVASIVE DETERMINATION OF HEMOGLOBIN AND HEMATOCRIT

(75) Inventors: Omar S. Khalil, Libertyville, IL (US); Xiaomao Wu, Gurnee, IL (US); Shu-jen Yeh, Grayslake, IL (US); Charles F. Hanna, Libertyville, IL (US); Stanislaw Kantor, Buffalo Grove, IL (US); Tzyy-Wen Jeng, Vernon Hills, IL (US)

(73) Assignee: Abbott Laboratoies, Abbott Park, IL (US)

( * ) Notice: Subject to any disclaimer, the term of this patent is extended or adjusted under 35 U.S.C. 154(b) by 0 days.

(21) Appl. No.: 09/566,415

(22) Filed: May 8, 2000

Related U.S. Application Data

(63) Continuation-in-part of application No. 09/080,470, filed on May 18, 1998, which is a continuation-in-part of application No. 09/419,461, filed on Oct. 15, 1999.

(51) Int. Cl.[7] .................................................. A61B 5/00
(52) U.S. Cl. ........................................ 600/322; 600/310
(58) Field of Search ................................ 600/309–310, 600/322–324, 316, 326; 356/39–42

(56) References Cited

U.S. PATENT DOCUMENTS

| | | |
|---|---|---|
| 3,628,525 A | 12/1971 | Polanyi et al. |
| 3,638,640 A | 2/1972 | Shaw |

(List continued on next page.)

FOREIGN PATENT DOCUMENTS

| | | |
|---|---|---|
| DE | 42 42 083 | 6/1994 |
| DE | 44 17 639 | 11/1995 |

(List continued on next page.)

OTHER PUBLICATIONS

Laufer, Jan, Rebecca Simpson, Matthias Kohl;, Matthias Essenpreis, and Mark Cope, "Effect of temperatureon the optical properties of ex vivo human dermis and subdermis" (1998) Phys. Med Biol. 43, p2479–2489.*
U.S. application Ser. No. 09/302,207, filed Apr. 29, 1999.

(List continued on next page.)

Primary Examiner—Eric F. Winakur
Assistant Examiner—Matthew Kremer
(74) Attorney, Agent, or Firm—David L. Weinstein

(57) ABSTRACT

A method for the determination of hemoglobin and hematocrit by means of an apparatus that is capable of controlling the temperature of a defined subcutaneous volume of human skin. The method involves a calculation of hemoglobin concentration and hematocrit value that takes into consideration the values of optical parameters of the sample at various pre-set temperatures. The apparatus and method employ steady state optical measurements of samples, such as, for example, human tissue, by means of a reflectance tissue photometer and localized control of the temperature of the sample. According to the method of this invention, an optical signal from a defined subcutaneous volume of human skin is measured as the temperature of this volume is controlled. The method and apparatus of this invention allow determination of hemoglobin concentration and hematocrit value non-invasively in a population of subjects having different skin colors by means of steady state reflectance measurements. The method of this invention for determination of hemoglobin concentration and hematocrit value is useful for monitoring patients, testing at the point of care, and screening for anemia. In contrast to other attempts in the prior art that rely on signals of cardiac pulses, the method of this invention has the advantage for the determination of analytes in weak cardiac pulse situations, such as, for example, in elderly patients.

23 Claims, 4 Drawing Sheets

U.S. PATENT DOCUMENTS

| | | |
|---|---|---|
| 4,223,680 A | 9/1980 | Jobsis |
| 4,259,963 A | 4/1981 | Huch |
| 4,432,365 A | 2/1984 | Leist |
| 4,655,225 A | 4/1987 | Dähne et al. |
| 4,882,492 A | 11/1989 | Schlager |
| 4,890,619 A | 1/1990 | Hatschek |
| 4,926,867 A | 5/1990 | Kanda et al. |
| 4,975,581 A | 12/1990 | Robinson et al. |
| 5,007,423 A | 4/1991 | Branstetter et al. |
| 5,057,695 A | 10/1991 | Hirao et al. |
| 5,086,229 A | 2/1992 | Rosenthal et al. |
| 5,115,133 A | 5/1992 | Knudson |
| 5,122,974 A | 6/1992 | Chance |
| 5,131,391 A | 7/1992 | Sakai et al. |
| 5,148,082 A | 9/1992 | Itou et al. |
| 5,187,672 A | 2/1993 | Chance et al. |
| 5,209,231 A | 5/1993 | Cote et al. |
| 5,218,207 A | 6/1993 | Rosenthal |
| 5,237,178 A | 8/1993 | Rosenthal et al. |
| 5,277,181 A | 1/1994 | Mendelson et al. |
| 5,297,548 A | 3/1994 | Pologe |
| 5,313,941 A | 5/1994 | Braig et al. |
| 5,321,265 A | 6/1994 | Block |
| 5,324,979 A | 6/1994 | Rosenthal |
| 5,337,745 A | 8/1994 | Benaron |
| 5,348,002 A | 9/1994 | Caro |
| 5,348,003 A | 9/1994 | Caro |
| 5,361,758 A | 11/1994 | Hall et al. |
| 5,362,966 A | 11/1994 | Rosenthal et al. |
| 5,372,136 A | 12/1994 | Steuer et al. |
| 5,379,764 A | 1/1995 | Barnes et al. |
| 5,383,452 A | 1/1995 | Buchert |
| 5,402,778 A | 4/1995 | Chance |
| 5,452,716 A | 9/1995 | Clift |
| 5,481,113 A | 1/1996 | Dou et al. |
| 5,492,118 A | 2/1996 | Gratton et al. |
| 5,492,769 A | 2/1996 | Pryor et al. |
| 5,497,769 A | 3/1996 | Gratton et al. |
| 5,499,627 A | 3/1996 | Steuer et al. |
| 5,515,847 A | 5/1996 | Braig et al. |
| 5,533,509 A | 7/1996 | Koashi et al. |
| 5,551,422 A | 9/1996 | Simonsen et al. |
| 5,553,615 A | 9/1996 | Carim et al. |
| 5,553,616 A | 9/1996 | Ham et al. |
| 5,596,987 A | 1/1997 | Chance |
| 5,665,530 A | 9/1997 | Oyamada et al. |
| 5,672,875 A | 9/1997 | Block et al. |
| 5,676,143 A | 10/1997 | Simonsen et al. |
| 5,692,503 A * | 12/1997 | Kuenstner ............... 600/322 |
| 5,720,284 A | 2/1998 | Aoyagi et al. |
| 5,725,480 A | 3/1998 | Oosta et al. |
| 5,770,454 A | 6/1998 | Essenpreis et al. |
| 5,782,755 A * | 7/1998 | Chance et al. ............ 600/322 |
| 5,823,951 A | 10/1998 | Messerschmidt |
| 5,873,821 A | 2/1999 | Chance et al. |
| 5,900,632 A * | 5/1999 | Sterling et al. ........ 250/339.03 |
| 5,935,062 A * | 8/1999 | Messerschmidt et al. ... 600/322 |
| 5,978,691 A * | 11/1999 | Mills ...................... 600/334 |
| 6,016,435 A * | 1/2000 | Maruo et al. ............. 600/316 |

FOREIGN PATENT DOCUMENTS

| | | |
|---|---|---|
| DE | 196 34 152 | 3/1998 |
| EP | 0 472 216 | 2/1992 |
| EP | 0 810 429 | 12/1997 |
| WO | 92/10131 | 6/1992 |
| WO | 92/20273 | 11/1992 |
| WO | 93/07801 | 4/1993 |
| WO | 93/13706 | 7/1993 |
| WO | 94/02837 | 2/1994 |
| WO | 94/05984 | 3/1994 |
| WO | 94/13199 | 6/1994 |
| WO | 95/20757 | 8/1995 |
| WO | 98/03847 | 1/1998 |
| WO | 99/39631 | 8/1999 |
| WO | 99/59464 | 11/1999 |

OTHER PUBLICATIONS

Graaff, et al., "Reduced light–scattering properties for mixtures of spherical particles: a simple approximation derived from Mie calculations", *Applied Optics*, vol. 31, No. 10, Apr. 1, 1992, pp. 1370–1376.

Bruulsema, et al., "Correlation between blood glucose concentration in diabetics and noninvasively measured tissue optical scattering coefficient", *Optics Letters*, vol. 22, No. 3, 1997, pp. 190–192.

Heinemann, et al., "Non–invasive continuous glucose monitoring in Type I diabetic patients with optical glucose sensors", *Diabetologia*, vol. 41, 1998, pp. 848–854.

Kienle, et al., "Spatially resolved absolute diffuse reflectance measurements for noninvasive determination of the optical scattering and absorption coefficients of biological tissue", *Applied Optics*, vol. 35, No. 13, 1996, pp. 2304–2314.

Marbach, et al., "Noninvasive Blood Glucose Asay by Near–Infrared Diffuse Reflectance Spectroscopy of the Human Inner Lip", *Applied Spectroscopy*, vol. 47, No. 7, 1993, pp. 875–881.

Qu, et al., "Monte Carlo Modeling Studies of the Effect of Physiological Factors and Other Analytes on the Determination of Glucose Concentration In Vivo by Near Infrared Optical Absorption and Scattering Measurements", *Journal of Biomedical Optics*, vol. 2, No. 3, 1997, pp. 319–325.

Quan, et al., "Glucose determination by a pulsed photoacoustic technique: an experimental study using a geletin-based tissue phantom", *Phys. Med. Biol.*, vol. 38, 1993, pp. 1911–1922.

Robbins, et al., "The Endocrine Pancreas", *Pathologic Basis of Disease*, $3^{rd}$ Edition, W. B. Saunders Company, 1984, pp. 972–990.

Tooke, et al., "Skin Microvascular Blood Flow Control in Long Duration Diabetics With and Without Complications", *Diabetes Research*, No. 5, 1987, pp. 189–192.

Wilson, et al, "Progress toward the Development of an Implantable Sensor for Glucose", *Clinical Chemistry*, vol. 38, No. 9, 1992, pp. 1613–1617.

Jobsis, "Noninvasive, Infrared Monitoring of Cerebral and Myocardial Oxygen Sufficiency and Circulatory Parameters", *Science*, vol. 198, 1977, pp. 1264–1267.

Gopinath, et al., "Near–infrared spectroscopic localization of intracranial hematomas", *Journal of Neurosurgery*, vol. 79, 1993, pp. 43–47.

Zhang, et al., "Investigation of Noninvasive in Vivo Blood Hematocrit Measurement Using NIR Reflectance Spectroscopy and Partial Least–Squares Regression", *Applied Spectroscopy*, vol. 54, No. 2, 2000, pp. 294–299.

Lin, et al., "Dynamics of tissue optics during laser heating of turbid media", *Applied Optics*, vol. 35, No. 19, 1996, pp. 3413–3420.

Laufer, et al., "Effect of temperature on the optical properties of *ex vivo* human dermis and subdermis", *Phys. Med. Biol.*, vol. 43, 1998, pp. 2479–2489.

Bruulsema, et al., "Optical Properties of Phantoms and Tissue Measured in vivo from 0.9–1.3 µm using Spatially Resolved Diffuse Reflectance", *SPIE Proceedings*, vol. 2979, 1997, pp. 325–334.

T. Shiga, et al., "Study of an Algorithm Based on Model Experiments and Diffusion Theory for a Portable Tissue Oximeter", *Journal of Biomedical Optics*, vol. 2, No. 2, Apr. 1997, pp. 154–161.

Jacques, et al., "Monte Carlo Modeling of Light Transport in Tissues", *Optical–Thermal Response of Laser–Irradiated Tissue*, edited by A.J. Welch and M.J.C. van Gemert, Plenum Press, New York, 1995, pp. 73–100.

Wilson, "Measurement of Tissue Optical Properties: Methods and Theories", *Optical–Thermal Response of Laser–Irradiated Tissue*, edited by A.J. Welch and M.J.C. van Gemert, Plenum Press, New York, 1995, pp. 233–274.

Morris, et al., "Basic Examination of Blood", *Clinical Diagnosis and Management by Laboratory*, 1996, pp. 549–559.

Lin, et al., "Dynamics of tissue reflectance and transmittance during laser irradiation", *SPIE Proceedings*, vol. 2134A Laser–Tissue Interaction V, 1994, pp. 296–303.

U.S. application Ser. No. 09/080,470, filed May 18, 1998.
U.S. application Ser. No. 09/366,084, filed Aug. 3, 1999.
U.S. application Ser. No. 09/419,461, filed Oct. 15, 1999.

* cited by examiner

METHOD AND DEVICE FOR THE NONINVASIVE DETERMINATION OF HEMOGLOBIN AND HEMATOCRIT

This invention is a continuation-in-part of U.S. application Ser. No. 09/080,470, filed May 18, 1998, and U.S. application Ser. No. 09/419,461, filed Oct. 15, 1999.

BACKGROUND OF THE INVENTION

1. Field of the Invention

This invention relates to devices and methods for the noninvasive determination of concentrations of hemoglobin and hematocrit in a human subject in vivo, particularly for the noninvasive determination of concentrations of hemoglobin and hematocrit in a human subject in vivo, where the temperature of a defined subcutaneous volume of a body part of the subject is controlled and varied between preset boundaries.

2. Discussion of the art

Non-invasive (hereinafter "NI") monitoring of analytes in the human body by optical devices and methods is an important tool in clinical diagnostics. NI monitoring techniques, which do not require obtaining a sample from the human body or inserting any instrumentation into the human body, have several advantages, including, but not limited to, ease of performing tests, reduction of pain and discomfort to the patient, and decreased exposure to potential biohazards.

The most established non-invasive optical technique is pulse oximetry. Oxygenation of blood in tissue and cerebral oxygen saturation can be measured, and the measurement can be used for clinical applications. See Jobsis, "Noninvasive, Infrared Monitoring of Cerebral and Myocardial Oxygen Sufficiency and Circulatory Parameters", Science, 198, 1264–67 (1977), and Shiga, et al., "Study of an Algorithm Based on Model Experiments and Diffusion Theory for a Portable Tissue Oximeter", J. Biomed. Optics; 2(2), 154–161 (1997).

Hemoglobin is the protein that transports oxygen. The hematocrit value provides an indication of the hemodynamics of the body. Non-invasive determination of the hemoglobin concentration (Hb) and the hematocrit value (Hct), when available, can be useful in blood donation centers, intensive care units, and surgical operation rooms. Non-invasive determination of the hemoglobin concentration and the hematocrit value can potentially be applied for diagnosis of anemia in infants and mothers, for localizing tumors, and for diagnosis of hematoma and internal bleeding. See S. Gopinath, et al., "Near-infrared spectroscopic localization of intracamerial hematomas", J. Neurosurgery, 79, 43–47 (1993).

Concentration of hemoglobin and the ratio of oxygenated hemoglobin to total hemoglobin in blood are important parameters for indicating the anemic state and wellness of a patient. Hemoglobin is a protein having a molecular weight of 64,500 daltons; thus, 1 gram of hemoglobin is equivalent to $1.55 \times 10^{-5}$ mole. The concentration of hemoglobin is expressed in g/dL. The hematocrit value is the ratio of volume of red blood cells to total blood volume, which comprises the volume of red blood cells and the volume of plasma. The hematocrit value is expressed as a percentage (i.e., volume percentage of red cells in whole blood). While measurement of concentration of hemoglobin provides an indication of the oxygen transport status of the patient, measurement of the hematocrit value provides an indication of concentration of both red blood cells for transport of oxygen and plasma for transport of nutrients. The measurement of the hematocrit value is particularly important when a change in body hemodynamics is expected, such as during operations of long duration, such as, for example, vascular and orthopedic surgery. Other applications of hematocrit measurement include the treatment of hemorrhage in accident victims and the monitoring of cancer patients undergoing chemotherapy. Yet another application of hematocrit measurement involves monitoring kidney dialysis patients to reduce the potential for incomplete dialysis or excessive dialysis of the patient. Incomplete dialysis leaves toxins behind. Excessive dialysis leads to shock.

The standard method currently used for measuring hematocrit value is an invasive method. Typically, a blood sample is obtained from a patient or a donor and centrifuged in a capillary tube to separate red blood cells from plasma. The length of the column in the capillary tube containing red blood cells and the total length of the column in the capillary tube containing both the red blood cells and the plasma are measured, and the ratio of these lengths is the hematocrit value (Hct). Other methods for determining the hematocrit value involve the use of a flow cytometer, where a known volume of blood is injected in a fluid stream and the number of red blood cells (RBC) and their mean volume is determined. The total volume of RBC is calculated and the hematocrit value is determined from the volume of the sample and the total RBC volume. Hemoglobin concentrations can be determined in vitro by a photometric method, where a blood sample is hemolyzed and the heme moiety is released from hemoglobin at a high pH condition. The absorption of this heme moiety is determined at wavelengths of 577 nm and 633 nm.

U.S. Pat. No. 5,227,181, U.S. Pat. No. 5,553,615, and U.S. Pat. No. 5,499,627 describe hematocrit monitoring devices that involve the use of light of a limited number of wavelengths. These patents do not involve a non-invasive measurement or an apparatus having a means for controlling the temperature of a sample. Because the spectral and optical properties of samples of human tissue depend on temperature in the near infrared region of the electromagnetic spectrum, hematocrit and blood oxygenation measurements in this region of the electromagnetic spectrum can be inaccurate, when temperature is not controlled. Zhang et al., "Investigation of Non-invasive in Vivo Blood Hematocrit Measurement Using NIR Reflectance Spectroscopy and Partial Least-Squares Regression", Applied Spectroscopy, vol. 54, no. 2, 294–299 (2000), discloses a method for non-invasively determining the hematocrit value in vivo during cardiac bypass surgery by employing a large number of wavelengths in the near-infrared region of the electromagnetic spectrum. Temperature of the patient was found to change during surgery. A high number of wavelengths and a partial least squares regression analysis were used in an effort to minimize the effect of temperature on the hematocrit value during the determination. Although the device and method described by Zhang et al. provide good calibration and prediction for a given patient during surgery, establishing a model to predict the hematocrit values across more than one patient was less successful. Systematic bias between patients was observed.

The effect of temperature on the scattering and absorption properties of tissue has been of interest in the art of non-invasive monitoring. Thermal effects of laser excitation, photocoagulation, and temperature effect on skin optics have been described in the art. See, for example, W-C. Lin et al., "Dynamics of tissue reflectance and transmittance during laser irradiation", SPIE Proceedings, 2134A Laser-Tissue Interaction V, 296–303 (1994); and W-C. Lin, "Dynamics of tissue optics during laser heating of turbid media", Applied Optics, Vol. 35, No. 19, 3413–3420 (1996). Other publications include J. Lauferet al., "Effect of temperature on the optical properties of ex vivo human dermis and subdermis", Phys. Med. Biol. 43 (1998) 2479–2489; and J. T. Bruulsema et al., "Optical Properties of Phantoms and Tissue Measured in vivo from 0.9–1.3 μm using Spatially Resolved Diffuse Reflectance", SPIE Proceedings 2979, 325–334 (1997).

U.S. Pat. Nos. 3,628,525; 4,259,963; 4,432,365; 4,890,619; 4,926,867; 5,131,391; and European Patent Application EP 0472216 describe oximetry probes having heating elements designed to be placed against a body part. U.S. Pat. No. 5,148,082 describes a method for increasing the blood flow in a patient's tissue during a photoplethysmography measurement by heating the tissue with a semiconductor device mounted in a sensor. U.S. Pat. No. 5,551,422 describes a glucose sensor that is brought to a specified temperature, preferably somewhat above normal body-temperature, with a thermostatically controlled heating system.

U.S. application Ser. No. 09/080,470, filed May 18, 1998, assigned to the assignee of this application, and WO 99/59464 describe a non-invasive glucose sensor employing a means for controlling the temperature of a sample. One purpose of controlling the temperature of a sample is to minimize the effect of physiological variables. U.S. application Ser. No. 09/098,049, filed Nov. 23, 1998, assigned to the assignee of this application, and U.S. application Ser. No. 09/419,461, filed Oct. 15, 1999, assigned to the assignee of this application, disclose the use of an optical element that is brought in contact with skin, the temperature of which skin is being controlled.

Although a variety of detection techniques have been disclosed in the art, there is still no commercially available device that provides hemoglobin and hematocrit measurements non-invasively with an accuracy that is comparable to measurements made by current commercially available invasive methods. Non-invasive measurements obtained by prior art methods are based on the assumption that the tissue comprises a single uniform layer that has a single uniform temperature. As a result, current approaches to non-invasive metabolite testing, such as hemoglobin determination or hematocrit monitoring, have not achieved acceptable precision and accuracy.

Thus, there is a need for improved apparatus and methods for non-invasive metabolite testing. It is desired that these methods and devices not be adversely affected by variations in skin temperatures and that they account for the effects of the various layers of skin. It is also desired that these methods and devices account for the effect of temperature on the optical properties of the various layers of skin.

SUMMARY OF THE INVENTION

This invention provides a method for the determination of hemoglobin and hematocrit by means of an apparatus that is capable of controlling the temperature of a defined subcutaneous volume of human skin. The method involves a calculation of hemoglobin concentration and hematocrit value that takes into consideration the values of optical parameters of the sample at various pre-set temperatures. The apparatus and method employ steady state optical measurements of samples, such as, for example, human tissue, by means of a reflectance tissue photometer and localized control of the temperature of the sample.

According to the method of this invention, an optical signal from a defined subcutaneous volume of human skin is measured as the temperature of this volume is controlled. The method and apparatus of this invention allow determination of hemoglobin concentration and hematocrit value non-invasively in a population of subjects having different skin colors by means of steady state reflectance measurements. The method of this invention for determination of hemoglobin concentration and hematocrit value is useful for monitoring patients, testing at the point of care, and screening for anemia. In contrast to other attempts in the prior art that rely on signals of cardiac pulses, the method of this invention has the advantage for the determination of analytes in weak cardiac pulse situations, such as, for example, in elderly patients.

In one aspect, this invention provides an improved method for the non-invasive determination of hemoglobin concentration or hematocrit value in a sample. The method comprises the steps of:

(a) setting the temperature of an area of skin of a body part to a first temperature, the first temperature being below the core temperature of the body, (b) performing an optical measurement in which at least one light introduction site on the surface of the skin is illuminated by a light beam at at least one wavelength and the light re-emitted from the underlying dermal layers is collected at at least one light collection site, the distance(s) between the at least one light introduction site and the at least one light collection site being selected to restrict the sampling depth of the body part to within the epidermis and dermis layer, the temperature being maintained at a constant value during the optical measurement, (c) setting the temperature of the area of skin of the body part to at least a second temperature that is within the physiological temperature range, (d) repeating step (b) at the at least second temperature, (e) determining a plurality of optical parameters at each temperature and determining the dependence of at least one of the aforementioned optical parameters on temperature, (f) establishing a calibration relationship that relates (1) at least one of the plurality of optical parameters at a given temperature and (2) the dependence of at least one of the plurality of optical parameters on temperature with the concentration of hemoglobin or the hematocrit value measured independently, and (g) determining the concentration of hemoglobin or the hematocrit value by means of a subsequent determination of the plurality of optical parameters at a given temperature and the dependence of the at least one of the aforementioned optical parameters on temperature and the calibration relationship established in step (f).

The temperatures at which the area of the skin is maintained during the measurements lie within the physiological temperature range, namely, 10° C. to 45° C. Preferably, temperatures are selected so as to assure comfort during the measurements. Accordingly, a preferred temperature range is 15° C. to 42° C., and a more preferred temperature range is 20° C. to 40° C.

The light used in the method of this invention can have a wavelength ranging from about 400 nm to about 1900 nm. It is possible to select a range of wavelengths that allows the use of one type of detector. Thus, a wavelength range of from about 400 nm to about 1100 nm can be used with a silicon detector, and a wavelength range of from about 700 nm to about 1900 nm can be used with an Indium/gallium arsenide detector. Hybrid detectors having wider wavelength ranges can be used to cover light having wavelengths in all or most of the visible and near infrared regions of the electromagnetic spectrum.

Spatially resolved diffuse reflectance measurement techniques can be used to perform the optical measurements of the method of this invention. The distance between the at least one light introduction site and the at least one light collection site preferably ranges from about 0.1 mm to about 10 mm, in order to allow collection of light re-emitted from the epidermis and dermis layers only and to minimize contributions from adipose tissue and muscle tissue. The use of small separation distances also allows for better control of the temperature of the tissue layer during the measurement.

Another method of performing the measurements of this invention is the selectable distance method, described in U.S. application Ser. No. 09/366,084, filed Aug. 3, 1999, incorporated herein by reference.

The volume of tissue subjected to temperature control and optical examination ranges from about 0.1 cubic millimeter to about 10 cubic millimeters, preferably from about 0.2 cubic millimeter to about 5 cubic millimeters, and more preferably from about 0.2 cubic millimeter to about 2 cubic millimeters.

Statistical methods for establishing a correlation between the optical signal obtained non-invasively and the measurement of hemoglobin concentration or hematocrit value determined invasively in order to establish a calibration relationship include, but are not limited to, linear least squares, partial least squares, and principal component analysis.

Another embodiment of the invention is an improved method for the determination of hemoglobin and hematocrit in human body that comprises:

(a) setting the temperature of an area of skin of a body part to a given temperature, the given temperature being below the core temperature of the body, (b) performing an optical measurement in which at least one light introduction site on the surface of the skin is illuminated by a light beam at at least one wavelength and the light re-emitted from the underlying dermal layers is collected at at least one light collection site, the distance(s) between the at least one light introduction site and the at least one light collection site being selected to restrict the sampling depth of the body part to within the epidermis and dermis layer, the given temperature being maintained at a constant value during the optical measurement, whereby the optical measurement generates a measurable signal, (c) correlating the measurable signal of step (b) with hemoglobin concentration or hematocrit value determined by an independent method to establish a calibration relationship, and (d) determining the concentration of hemoglobin or the hematocrit value from a signal from a subsequent optical measurement and the calibration relationship of step (c).

This invention provides several advantages over the prior art. The measurement method does not rely on the cardiac pulse, and thus is more suitable for the elderly and for individuals having poor peripheral circulation. Improvement in the measurement of the concentration of hemoglobin and the hematocrit value is brought about by changing light penetration depth in a defined volume of tissue and by sampling blood vessels deeper in the skin, without the need to exert pressure or raise temperature to alter flow of blood. In one embodiment, the method involves measurement of a defined volume of the dermis layer of the tissue at a constant temperature below the body core temperature, thereby avoiding the effects of temperature fluctuation on the data. This embodiment allows improved correlation with venous hemoglobin concentration and hematocrit values, even though simple instrumentation is employed.

DETAILED DESCRIPTION OF THE INVENTION

Figure 1:
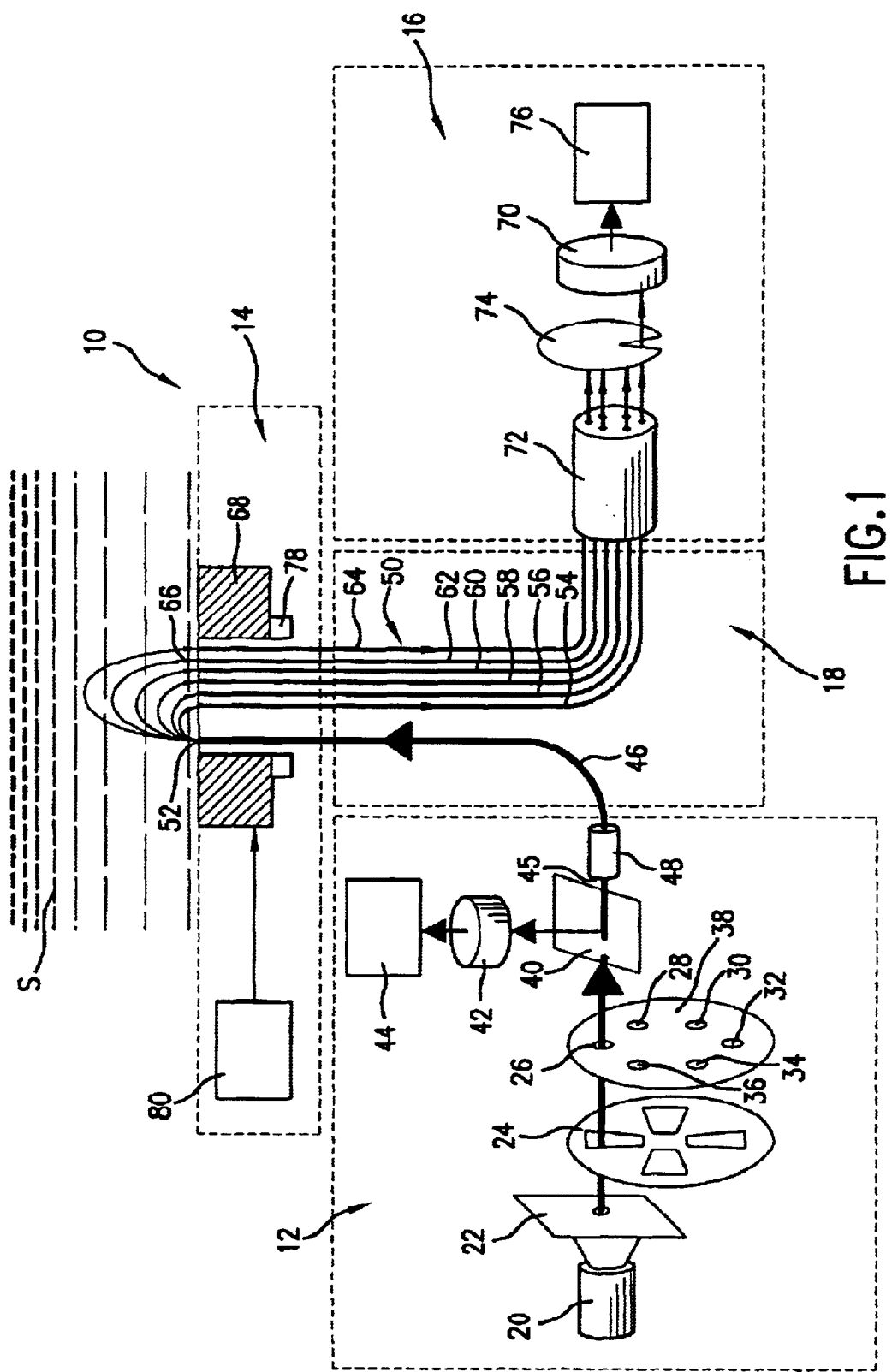
FIG. 1 is a schematic view of an optical system suitable for use in the method of this invention

As used herein, the expression "tissue optics" refers to the study of light propagation in biological tissues. The expression "optical properties" refers to the absorption, scattering, emission, reflectance, and depolarization properties of biological tissues. The expression "optical parameter" refers to a parameter that describes and defines an optical property of a medium and its components. Examples of optical parameters include, but are not limited to, absorption coefficient, scattering coefficient, anisotropy factor, transport optical mean free path, and extinction coefficient of analytes. The expression "scattering media" refers to media that both scatter light and absorb light. The expression "absorption coefficient" (i.e., $\mu_a$) refers to the probability of light absorption per unit path length, which is equal to $2.303\, \epsilon \cdot C$ in $cm^{-1}$, where, $\epsilon$ is molar extinction coefficient and C is the molar concentration. The expression "scattering coefficient" (i.e., $\mu_s$) refers to the probability of light scattering per unit path length, which is equal to $\alpha \rho$ in $cm^{-1}$, where, $\alpha$ is scattering cross section and $\rho$ is the number density of scattering centers. The expression "anisotropy factor" (i.e., g) refers to the average cosine of the scattering angle for a multiply scattered photon. The expression "reduced scattering coefficient" (i.e., $\mu_s'$) refers to the probability of equivalently isotropic (uniform in all directions) scattering per unit path length. The reduced scattering coefficient is related to the scattering coefficient $\mu_s$ and the anisotropy factor g by the relationship $\mu_s' = (1-g)\mu_s$. The expression "light penetration depth" (i.e., $\delta$) represents the depth at which light intensity in the tissue is attenuated to 1/e of its original value. Light penetration depth is determined by the rate of decay of intensity of light in scattering media with respect to the path traveled by the light in the same direction as the incident light. The effective attenuation coefficient $\mu_{eff}$ is the reciprocal of the light penetration depth δ, i.e., $\delta=1/\mu_{eff}=1/\sqrt{(3\mu_a(\mu_a+\mu_a'))}$. As described in U.S. application Ser. No. 09/419,461, filed Oct. 15, 1999, a change in the temperature at the measurement site results in a change in light penetration depth in human skin; light penetration depth increases as the temperature is lowered below the body core temperature. The expression "change in light penetration depth as a function of temperature $\Delta\delta_T$" is defined as the difference in the value of the calculated light penetration depth in tissue at two preset temperatures, i.e. $\Delta\delta_T=\delta(T_1)-\delta(T_2)$. Alternatively, "change in light penetration depth as a function of temperature $\Delta\delta_T$" is defined as the product of the rate of change in light penetration depth as a function of temperature and the temperature interval in the measurement, i.e. $\Delta\delta_T=(\partial\delta/\partial T)\cdot\Delta T$.

The expression "Monte Carlo simulation" refers to a numerical method that can be used to statistically describe photon propagation in scattering media. The expression "diffuse reflectance" (reflectance therein unless specified otherwise) refers to measurement of light that is re-emitted from a sample at all angles different from the direction of the incident light, and over an area wider than the area where the incident light is introduced into the sample. The expressions "spatially resolved scattering" or "spatially resolved diffuse reflectance" and "localized reflection" refer to a measurement of light that is re-emitted from a sample and collected at several light collection sites at specific distances from a light introduction site. Alternatively, these expressions can refer to the light collected at a given light collection site on the sample boundary as a result of introducing light at discrete light introduction sites located on the same boundary at a set of defined distances from the light collection site. In both instances, $\mu_{eff}$, $\mu_a$ and $\mu_s'$ are calculated from the intensity distribution of the re-emitted light with respect to distances, i.e., the re-emitted light intensity at a multiplicity of sampling distances. The expressions "re-emitted light" and "reflected light" are used synonymously herein, as are the expressions "reflectance" and the "intensity of re-emitted light", unless otherwise indicated. The expression "frequency domain measurement" refers to a measurement of light involving the phase angle and/or the amplitude change of modulated incident light, at a given separation distance of a light introduction site from a light collection site, as the light transverses a scattering medium. The expression "beam of light" refers to a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber.

The expression "light introduction site" means a location on the surface of a sample, e.g., a body part, tissue, or the like, at which light is injected or introduced into the sample. The source of the light can be located at the light introduction site or can be located remote from the light introduction site. If the source of light is located remote from the light introduction site, the light must be transmitted to the light introduction site by light transmitting means, such as, for example, optical fibers. The expression "illuminating element" means a component located at the light introduction site that delivers light to the sample, e.g., a body part, tissue, or the like. The illuminating element is typically an optical fiber that transmits light from a source of light to the light introduction site. However, if the source of light is located at the light introduction site, the source of light can be the illuminating element. The expression "light collection site" means a location on the surface of a sample, e.g., a body part, tissue, or the like, at which light that is re-emitted from the sample is collected for measurement. The detector, which measures the intensity of the re-emitted light, can be located at the light collection site or can be located remote from the light collection site. If the detector is located remote from the light collection site, the light must be transmitted to the detector by light transmitting means, such as, for example, optical fibers. The expression "light collecting element" means a component located at the light collection site that collects light that is re-emitted from the sample, e.g., a body part, tissue, or the like. The light collecting element is typically an optical fiber that transmits light from the light collection site to a detector. However, if the detector can be located at the light collection site, the detector can be the light collecting element. The distance between a light introduction site and a light collection site, as measured along the surface of a sample, is defined as the "sampling distance". For a given sample, the sampling distance determines the mean distance from the surface of the sample into the interior of the sample at which the scattering and absorption events contribute to the measured re-emitted light. Such mean distance is hereinafter referred to as the "sampling depth", which is a function of the sampling distance. According to this invention the sampling depth in human skin is modified by changing the temperature of the tissue; sampling depth increases as the temperature is lowered within the physiological temperature range of the body.

As used herein, the expression "physiological temperature range" of a biological sample means the temperature range over which the biological activity of the sample is maintained, without irreversible change in the its optical or biological properties as a result of changing temperature. As used herein, the expression "body core temperature" means the temperature of the interior of the body remote from the extremities of the body. Rectal temperature and esophageal temperature represent body core temperature. For normal human beings, body core temperature is 37±1° C.

One embodiment of this invention involves a method for the non-invasive determination of hemoglobin concentration or hematocrit value in human tissue. This method comprises the steps of:

(a) setting the temperature of an area of skin of a body part to a first temperature, the first temperature being below the core temperature of the body, (b) performing an optical measurement in which at least one light introduction site on the surface of the skin is illuminated by a light beam at at least one wavelength and the light re-emitted from the underlying dermal layers is collected at at least one light collection site, the distance(s) between the at least one light introduction site and the at least one light collection site being selected to restrict the sampling depth of the body part to within the epidermis and dermis layer, the temperature being maintained at a constant value during the optical measurement, (c) setting the temperature of the area of skin of the body part to at least a second temperature that is within the physiological temperature range, (d) repeating step (b) at the at least second temperature, (e) determining a plurality of optical parameters at each temperature and determining the dependence of at least one of the aforementioned optical parameters on temperature, (f) establishing a calibration relationship that relates (1) at least one of the plurality of optical parameters at a given temperature and (2) the dependence of at least of the plurality of optical parameters on temperature with the concentration of hemoglobin or the hematocrit value measured independently, and (g) determining the concentration of hemoglobin or the hematocrit value by means of a subsequent determination of the plurality of optical parameters at a given temperature and the dependence of the at least one of the aforementioned optical parameters on temperature and the calibration relationship established in step (f).

The temperatures at which the area of the skin is maintained during the measurements lie within the physiological temperature range (10° C. to 45° C.). Preferably temperatures are selected to assure comfort during the measurements, thus a preferred range is 15° C. to 42° C. and a more preferred range is 20° C. to 40° C.

The wavelength of light used in this invention ranges from 400 nm to 1900 nm. It is possible to select wavelength ranges that allow the use of a one type of detector. Thus a range from 400 to 1100 nm can be used with a silicon detector and a range from 700 to 1900 nm can be used with an Indium/gallium arsenide detector. Hybrid detectors with wider wavelength ranges can be used to cover all or most of the visible and near infrared spectrum.

One method of performing the optical measurements of this invention is spatially resolved diffuse reflectance measurement. Distance between the light introduction site and the light measurement site is between 0.1 mm to 10 mm, in order to allow for detecting light re-emitted from the epidermis and dermis layers only and to minimize the contributions from adipose tissue and muscle layers. This also allows for better control of the temperature of the tissue layer during the measurement. Another method of performing the measurement of this invention is the selectable distance method described in U.S. application Ser. No. 09/366,084, filed Aug. 3, 1999, incorporated herein by reference.

Methods for establishing the correlation between the noninvasive optical signal and the invasive measurement of hemoglobin or hematocrit in order to establish a calibration relationship include, but are not limited to, the linear least squares, partial least squares, or principal component analysis.

Another embodiment of the invention involves a method for the determination of hemoglobin concentration or hematocrit value in human body. The method comprises the steps of:

(a) setting the temperature of an area of skin of a body part to a given temperature, the given temperature being below the core temperature of the body, (b) performing an optical measurement in which at least one light introduction site on the surface of the skin is illuminated by a light beam at at least one wavelength and the light re-emitted from the underlying dermal layers is collected at at least one light collection site, the distance(s) between the at least one light introduction site and the at least one light collection site being selected to restrict the sampling depth of the body part to within the epidermis and dermis layer, the given temperature being maintained at a constant value during the optical measurement, whereby the optical measurement generates a measurable signal, (c) correlating the measurable signal of step (b) with hemoglobin concentration or hematocrit value determined by an independent method to establish a calibration relationship, and (d) determining the concentration of hemoglobin or the hematocrit value from a signal from a subsequent optical measurement and the calibration relationship of step (c).

Correlation between the noninvasive optical signal and the invasive measurement of hemoglobin or hematocrit in order to establish a calibration relationship can be calculated by one of the following methods: linear least squares, partial least squares, or principal component analysis.

Spatially resolved diffuse reflectance measurements have been previously described in prior art. See for example, B. Wilson, "Measurement of Tissue Optical Properties: Methods and Theories" in *Optical-Thermal Response of Laser-Irradiated Tissue*, A. J. Welch and M. C. C. Van Gemert, eds., Plenum Press (New York, N.Y.: 1995), pages 233–261. The use of Monte Carlo simulations to derive the values of optical parameters has been described in prior art. See for example S. L. Jacques and L. Wang "Monte Carlo Modeling of Light Transport in Tissues", in *Optical-Thermal Response of Laser-Irradiated Tissue*, A. J. Welch and M. C. C. Van. Gemert, eds., Plenum Press (New York, N.Y.: 1995), pages 73–100. The use of spatially resolved diffuse reflectance and Monte Carlo simulations for the determination of optical parameters, in a restricted volume of tissue under temperature control, was described in the art (see WO 99/59464).

In order to appreciate the effects of temperature variations on non-invasive measurements, it may be helpful to review the theoretical description of light propagation in tissues. A discussion of optical properties of tissue and the effect of these properties on light scattering and absorption is provided below. The dependence of NI measurements on temperature of the tissue is also illustrated, and preferred embodiments for controlling the temperature of NI measurements are described.

Light fluence within a turbid sample such as a human tissue sample, where light may undergo scattering events, is described in the art by the following formula:

$$I = I_o \exp(-\mu_{eff} z) \tag{1}$$

where $I_o$ represents the intensity of the incident light, I represents the intensity of the light at a depth z from the surface of the sample, and $\mu_{eff}$ is defined as:

$$\mu_{eff} = \sqrt{(3 \mu_a[\mu_a + \mu_s(1-g)])} = \sqrt{(3 \mu_a(\mu_a + \mu_s'))}. \tag{2}$$

Penetration of light into the tissue is expressed by the light penetration depth, δ, which is determined by the rate that intensity of light decays in turbid media along the direction of light introduction. The light penetration depth is the reciprocal of the effective attenuation coefficient $\mu_{eff}$ wherein:

$$\delta = 1/\mu_{eff} = 1/\sqrt{(3 \mu_a(\mu_a + \mu_s'))} \tag{3}$$

Light penetration depth is a statistical representation of the distance measured from the surface of the sample to the interior of the sample at which intensity of light is attenuated to 1/e of its incident value, where e is the base of the natural logarithm. The distance is measured along the direction of incident light. Light penetration depth corresponds to the depth in tissue, z, wherein 37% of the intensity of incident light is maintained. According to equation (1), $$I(\text{when } z=\delta) = I_o/e = 0.37 I_o \tag{4}$$

Because the value of δ depends on both $\mu_a$ and $\mu_s'$, an increase in either of $\mu_a$ or $\mu_s'$ will lead to a decrease in the light penetration depth δ in the tissue. Conversely, a decrease in the value of either of these two coefficients will lead to an increase in the light penetration depth in the tissue.

When tissue samples are irradiated with light in the visible and near-infrared regions of the electromagnetic spectrum, where the dimension (size) of the scattering material (particles, such as cells) is close to the magnitude of the wavelength of the light, the reduced scattering coefficient, $\mu_s'$, can be expressed using Mie theory as follows:

$$\mu_s' = 3.28\pi a^2 \pi (2\pi a n_{ex}/\lambda)^{0.37}(m-1)^{2.09} \quad (5)$$

where ρ represents volume density, i.e., the number of particles per unit volume; "a" represents the radius of the scattering particle (e.g., cells, mitochondria, or collagen fibrils); $n_{ex}$ represents the refractive index of the medium (interstitial fluid); $m=(n_{in}/n_{ex})$, the ratio of the refractive index of the scattering particle $n_{in}$ to the refractive index of the medium $n_{ex}$; and λ represents the wavelength of the light. See Graaff et al., "Reduced light-scattering properties for mixtures of spherical particles: a simple approximation derived from Mie calculations", Applied Optics, Vol. 31, No. 10, 1370–1376 (1992).

For incident light having a given wavelength, $\mu_s'$ varies directly with either the cell size, "a", or the refractive index ratio "m", as shown in Equation (5). Because the refractive index of the scattering particles, $n_{in}$, remains relatively constant, $\mu_s'$ is influenced primarily by $n_{ex}$ and particle radius "a".

Methods for determining $\mu_{eff}$, $\mu_s'$ and $\mu_a$ are known in the art. One of these methods involves the measurement of diffuse reflectance of the skin tissue. In a diffuse reflectance measurement, the measured reflectance is a function of the reduced scattering coefficient $\mu_s'$, the absorption coefficient $\mu_a$, the refractive index of the scattering medium, and the refractive index of the surrounding layer, which is usually air.

One method of measuring the absorption and scattering coefficients of tissue is referred to as spatially resolved diffuse reflectance, wherein the intensity of re-emitted light is a function of the distance of the light introduction site from the light collection site on the surface of the sample. In this method, the intensity of the light re-emitted from a sample is measured at several distances on the surface from the site at which light is introduced into the sample. Under these conditions, intensity of the re-emitted light is related to the distance of the light introduction site from the light collection site by the relationship:

$$R(r) = K_o[\exp(-\mu_{eff}r)]/r \quad (6)$$

$$\text{Log}[r \cdot R(r)] = \text{Log}(K_o) - \mu_{eff} r \quad (7)$$

where R(r) represents the intensity of light re-emitted from a sample at a light collection site, which is separated from the light introduction site by a distance r, $K_o$ is a constant, $\mu_{eff}$ is the effective attenuation coefficient, and $\text{Log}(K_o)$ represents the natural logarithm of a number $K_o$. Equation (7) can be used for calculating the change in $\mu_{eff}$, and hence the light penetration depth δ, as a function of temperature of the tissue. Other methods can be used to determine $\mu_{eff}$, such as, for example, frequency domain measurements, and diffuse reflectance measurements.

The ability to accurately determine $\mu_s'$ and $\mu_a$ separately by means of Equations (6) or (7) depends on the use of a diffusion theory approximation and requires a certain ratio of the scattering coefficient to the absorption coefficient ($\mu_s' \gg \mu_a$). Accordingly, the wavelength range of the measurement must be limited to a range where this relationship holds. The diffusion theory approximation also requires a large separation (sampling distance) between the light introduction site and the light collection site; hence, samples having large mass, such as the skull, the biceps, or the calves, are required. See U.S. Pat. No. 5,492,118. The diffusion theory is also based on the assumption that human tissue is a homogeneous medium, which is contrary to what is known in the medical art. Several layers of the skin are histologically distinguishable, i.e., the epidermis (including the stratum corneum), the dermis, and subcutaneous tissues. Each layer ranges from tens to hundreds of micrometers in thickness.

In a preferred embodiment of this invention, the distance between the light introduction site and the light collection site (or sites) is kept small (under 3 mm) to confine observation of light interaction with tissue to approximately 1 to 10 mm³, inclusive. The small sampling distance allows temperature to be controlled and modulated over a small volume of tissue. The use of a small sampling distance limits the use of the diffusion theory approximation to aid in calculating optical parameters of tissue.

Figure 2:
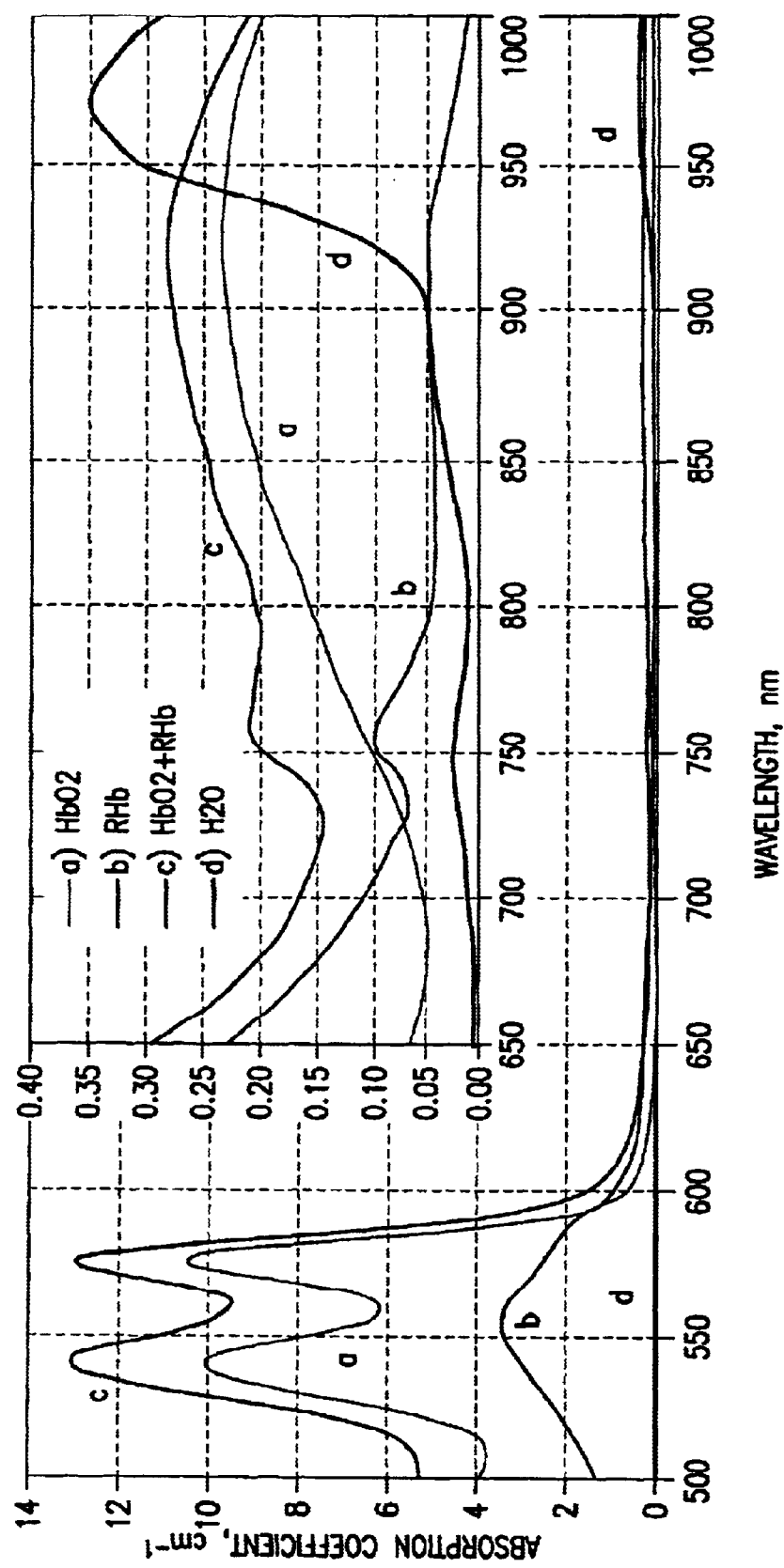
FIG. 2 is an illustration showing the absorption spectra of reduced hemoglobin (RHb), oxygenated hemoglobin ($HbO_2$), and water in the near-infrared region of the electromagnetic spectrum, calculated from published data and expressed as the absorption coefficient $\mu_a = 2.303\, \epsilon \cdot C$ ($cm^{-1}$).

The absorption spectra of oxygenated hemoglobin, deoxy-hemoglobin, and water in the near-infrared region of the electromagnetic spectrum are shown in FIG. 2. Each spectrum is expressed as absorption coefficient ($\mu_a = 2.303 \epsilon \cdot C$). The spectra were derived from published values of the extinction coefficient (ε) with the estimate of the nominal concentration of hemoglobin [C] in human tissue of 14.6 g/dL.

An optical probe device is described in WO 99/59464. The device can be used to determine the absorption and scattering coefficients of tissue. The distances between the illuminating element and the light collecting elements, which determine the sampling depth in tissue, are given in TABLE 1.

TABLE 1

| Collection fiber | $r_1$ | $r_2$ | $r_3$ | $r_4$ | $r_5$ | $r_6$ |
|---|---|---|---|---|---|---|
| Sampling Distance, mm | 0.44 | 0.78 | 0.92 | 1.22 | 1.40 | 1.84 |

The average values for the absorption and scattering coefficients, the mean free path, and the light penetration depth, δ, in human forearm skin of different subjects are set forth in TABLE 2. Measurements were performed at 34° C. When the collection fiber separations of TABLE 1 are used, the light penetration depth ranges from 0.72 mm when light having a wavelength of 550 nm propagates through the skin to 2.04 mm when light having a wavelength of 900 nm propagates through the skin. Using the absorption and scattering coefficient data in WO 99/59464, it is possible to calculate the volume of tissue that is illuminated and from which the re-emitted light is collected for detection. The maximum volume at a wavelength of 900 nm is 1.83 mm³. This volume of tissue illuminated will increase at longer wavelengths and can reach a volume up to 5.48 mm³.

TABLE 2

| Wavelength → | 550 nm | 590 nm | 650 nm | 750 nm | 800 nm | 900 nm |
|---|---|---|---|---|---|---|
| Optical constant ↓ | | | | | | |
| $(\mu_s' + \mu_a)$ (mm⁻¹) | 1.6 | 1.4 | 1.1 | 1.0 | 0.9 | 0.8 |
| Mean free path (mm) | 0.62 | 0.72 | 0.88 | 1.03 | 1.1 | 1.23 |
| Penetration depth (mm) | 0.72 | 0.92 | 1.42 | 1.67 | 1.92 | 2.04 |
| Maximum tissue volume | | | | | | |

TABLE 2-continued

| Wavelength → | 550 nm | 590 nm | 650 nm | 750 nm | 800 nm | 900 nm |
|---|---|---|---|---|---|---|
| sampled at 1 δ (mm³) | 0.65 | 0.82 | 1.27 | 1.50 | 1.72 | 1.83 |
| Maximum tissue volume sampled at 3 δ (mm³) | 1.94 | 2.47 | 3.82 | 4.50 | 5.16 | 5.48 |

When illuminating this small volume and collecting light re-emitted therefrom, only light re-emitted from the top layers of the skin will significantly contribute to the signal. Thus, the epidermis and upper dermis will be optically interrogated. Tissue, blood capillaries, and upper plexus will interact with the light. Tissue and blood vessels in this limited, temperature-controlled volume will affect the spectral properties of the light, and signals from these components will subsequently be detected.

The classical least square regression (CLSQ) method can be used to establish calibration and validation models. Assuming that each concentration of each analyte modulates the optical parameters linearly, the concentration of analyte can be expressed as a linear function of optical parameters, i.e., $$[Analyte] = a_0 + \sum_{i=1}^{n} a_i \cdot Optical\_Parameter_i \qquad (8)$$

where, [Analyte] represents the concentration of hemoglobin or the value of the hematocrit, and Optical_Parameter represents the $i^{th}$ optical parameter obtained from the measurement, and $a_0, a_1, a_2, \ldots$ represent coefficients to be determined from the regression.

The performance of a model was judged by the standard error of calibration (SEC) and the calibration correlation coefficient ($r_c$). The optical parameters selected and the number of the terms in the linear model were determined by the highest value of $r_c$ and the lowest value of SEC. A four-term model generally provided optimal results. A model employing two or three terms resulted in significantly worse values of $r_c$ and SEC. When more than four terms were used in a model, the model became unstable, probably due to overfitting. Criteria for a reasonably successful model was arbitrarily established as a model that yielded a value of r greater than 0.72.

The ability of a model derived by the classical least square regression to predict the concentration of hemoglobin and the value of hematocrit was tested for validity by means of the so-called leaving-one-out cross validation method. This validation method is particularly advantageous when the number of samples is limited. In a test population, a given sample is selected first and designated as the sample to be left out of the calibration. A model is calibrated using the optical measurement data for the remaining samples along with the reference values of hemoglobin or hematocrit determined in vitro. The model is then used to predict the concentration for the first sample, i.e., the sample that is left out. Then, the same procedure is applied sequentially to each of the remaining samples, one at a time. A predicted value of the concentration of the analyte is thereby obtained for each sample in the population. The standard error of prediction (SEP) and the prediction correlation coefficient $r_p$ (based on comparison between the predicted values of hemoglobin and hematocrit and the reference values of hemoglobin and hematocrit) are more stringent criteria of model performance than are the calibration criteria alone ($r_c$ and SEC) for the non-invasive determination of hemoglobin and hematocrit.

According to an embodiment of the invention, the change in temperature leads to a change in the depth that the light penetrates into the sample. When light is introduced into a biological sample at the surface thereof, such as the skin of a body part, the light is diffusely reflected. This diffusely reflected light is collected at one or more light collection sites located on the surface of the biological sample at one or more distances from the light introduction site. A detector measures the intensity of the collected light. For a given light collection site at a specified distance from the light introduction site, light will traverse a path at a given depth in the biological sample. This depth, defined as the sampling depth, is associated with a specific sampling distance. However, this sampling depth in a biological sample varies with temperature, and thus the light traverses different depths and/or different blood vessels in the dermal layer. By inducing a temperature change within the physiological temperature range of the human body during the steps of optical measurement, and by allowing for a contribution of change in light penetration depth with temperature in the CLSQ regression equation, one can improve the determination of hemoglobin concentration and value of hematocrit in the human body.

U.S. application Ser. No. 09/419,461, filed Oct. 15, 1999, incorporated herein by reference, describes a method for modulating depth of light penetration in tissue and discloses diagnostic applications employing the step of modulating the depth of light penetration. The effect of varying the temperature between two pre-set values (between 38° C. and 22° C.) on the optical parameters of human skin was described in U.S. application Ser. No. 09/419,461, filed Oct. 15, 1999. TABLE 3 shows the data for the change in optical parameters as measured from the forearm of human volunteers at two temperatures. The light had a wavelength of 590 nm. A significant change in light penetration depth is evident.

TABLE 3

| | 22° C. | | | 38° C. | | | |
|---|---|---|---|---|---|---|---|
| Subject No. | $\mu_a$ (1/cm) | $\mu'_s$ (1/cm) | δ (mm) | $\mu_a$ (1/cm) | $\mu'_s$ (1/cm) | δ (mm) | Δδ (μm) |
| 1 | 2.209 | 8.204 | 1.20 | 2.825 | 8.763 | 1.01 | 195 |
| 2 | 2.495 | 9.059 | 1.08 | 3.253 | 10.176 | 0.87 | 202 |
| 3 | 2.143 | 8.768 | 1.19 | 2.698 | 9.045 | 1.03 | 168 |
| 4 | 2.335 | 9.022 | 1.12 | 2.736 | 9.620 | 0.99 | 128 |
| 5 | 2.061 | 9.673 | 1.17 | 2.493 | 9.945 | 1.04 | 137 |
| 6 | 2.524 | 11.060 | 0.99 | 3.184 | 11.444 | 0.85 | 140 |
| 7 | 2.442 | 8.849 | 1.10 | 2.819 | 9.223 | 0.99 | 109 |
| 8 | 1.404 | 9.812 | 1.45 | 1.974 | 11.015 | 1.14 | 315 |
| 9 | 2.892 | 8.760 | 0.99 | 3.327 | 9.252 | 0.89 | 102 |

We have discovered that temperature changes affect the absorption coefficient of tissue in one or both of the following ways:

(1) Decreasing temperature decreases flow of blood to the volume of skin tissue monitored during the measurement. This decrease in blood flow in turn lowers the value of absorption coefficients at wavelengths of hemoglobin and water absorption in the 500 nm to 1100 nm region of the electromagnetic spectrum.

(2) Decreasing temperature affects temperature dependent change in the absorption coefficient of water in the 900 nm to 2500 nm region of the electromagnetic spectrum. The absorption properties of water are known to be very sensitive to temperature changes.

Changes in temperature also cause changes in the scattering properties of tissue. As described in U.S. application Ser. No. 09/419,461, filed Oct. 15, 1999, a decrease in temperature results in a decrease in the scattering coefficient, and, hence, a decrease in the reflectance of human skin.

Change in temperature affects both the absorption and scattering properties of human skin by affecting blood flow in the dermis layer and by affecting water absorption bands and the scattering coefficient of tissue. Change in δ as temperature is lowered is associated with change in blood content (hemoglobin and plasma) in the volume of tissue probed by the light beam. Change in light penetration depth (δ) can be achieved by two mechanisms that occur concurrently, because $\delta = 1/\sqrt{3\mu_a(\mu_a + \mu_s')}$. First, a decrease in blood flow to the subsurface capillaries, i.e. a decrease in $\mu_a$ of the top layers, can lead to an increase in δ. Secondly, a decrease in the scattering coefficient as a function of temperature can also lead to an increase in δ. An increase in light penetration depth allows the sampling of the larger blood vessels in the deeper dermis layers: Optical measurement of absorption and scattering of the skin at varying temperatures is equivalent to measuring the signal generated from different depths of tissue, each different depth containing a different volume of blood. Such a change in blood volume contributes to the fitting equation and improves correlation with the hemoglobin concentration and the hematocrit value in venous blood.

EXAMPLES

The following non-limiting examples further illustrate the present invention.

Example 1

A temperature-controllable localized reflectance tissue photometer (TCLRTP) having the capability of controlling the temperature of the sample and varying the temperature of the sample within a small depth in the tissue was constructed for use in the examples described below. Details of the breadboard construction are described in WO 99/59464, incorporated herein by reference. Briefly, the apparatus 10 comprises a light source module 12, an optical probe module 14, and a signal detection module 16 as shown schematically in FIG. 1. These three modules were interconnected through a branched optical fiber bundle 18.

A 5-watt incandescent lamp 20 (Model L1041, Gilway Technical Lamp, Woburn, Mass.) powered by a constant voltage source (not shown) delivered nearly uniform light through a 2-mm diameter iris 22. Light was chopped at 150 Hz by an optical chopper 24 coupled to a lock-in amplifier (not shown). The beam was then collimated and passed through one of six 10-nm band pass filters 26, 28, 30, 32, 34, and 36 having individual central wavelengths at 590 nm, 650 nm, 750 nm, 800 nm, 900 nm, and 950 nm, respectively, assembled in a filter wheel 38. A portion of the filtered light was diverted by a beam splitter 40 and focused onto a silicon photodiode 42 (Model S-2386-44K 6C, Hamamatsu, Hamamatsu-city, Japan) and a pre-amplifier 44 to generate a reference signal, which was used to correct for fluctuations in lamp intensity. The remainder of the filtered light beam was re-focused onto one end 45 of an illuminating element 46 (an optical fiber) housed at the source tip 48 of the fiber bundle 50. The filters 26, 28, 30, 32, 34, and 36 were selected to cover critical wavelength bands in of the spectra of hemoglobin and water.

The other end 52 of the illuminating element 46 and the ends of six light collecting elements 54, 56, 58, 60, 62, and 64 (optical fibers) proximal to the skin "S" were mounted in a common tip 66, situated at the center of a 2-cm diameter temperature-controlled disc 68. The common tip 66 and the temperature-controlled disc 68 are parts of the optical probe 14. All of the fibers 54, 56, 58, 60, 62, and 64 were made of clad silica, and they had a diameter of 400 μm (Fiberguide Industries, Stirling, N.J.). The distance from the center of the proximal end of each light collecting element 54, 56, 58, 60, 62, and 64 to the center of the end 52 of the illuminating element 46 defined the sampling distances $r_1$ through $r_6$ of this apparatus, which are listed in TABLE 1.

The light re-emitted form the skin was collected by the light collecting fibers 54, 56, 58, 60, 62, and 64 and transmitted to the detection module 16. A single silicon photodiode 70 (same type as the reference photodiode 42) in detection module 16 measured the light intensity transversely from the six light collecting fibers 54, 56, 58, 60, 62, and 64. The end of each light collecting fiber distal to the skin "S" was located in a detection tip 72. A rotating shutter 74 selected the optical signal from each light collecting fiber fiber, one at time, thereby allowing each signal to be detected by the photodiode 70 and a pre-amplifier 76. A lock-in amplifier Model SR830 DSP, Stanford Research Systems, Sunnyvale, Calif., (not shown) coupled to the optical chopper 24 at the source module 12, processed the pre-amplified signals.

The TCLRTP probe was mounted on the left arm of a standard blood-drawing chair. The subject sat in the chair with the left arm resting in a cradle against the spring-loaded optical detection head, which was pressed against the dorsal side of the subject's forearm at a constant force of 100 grams (approximately 30 grams per cm²). A thermoelectric cooling/heating element 78 (Model SP1507-01AC, Marlow Industries, Dallas, Tex.) and a controller/power supply unit 80 (Marlow Industries, SE5000-02) controlled the temperature of the disc 68, which was placed in contact with the skin. A personal computer employing LabView™ (version 5.1, National Instruments, Austin, Tex.) software program controlled the filter wheel 38, the rotating shutter 74, and the temperature setting via the controller 80. The personal computer and its accompanying software also managed acquisition of data.

A calibration algorithm was used to correct for fluctuation of the lamp, spectral output of the lamp, spectral response of the detector, relative light throughput of each fiber, and dark current of the system. Accordingly, the magnitude of the reflectance signal thus obtained differs from its true value only by a common multiplicative factor that is unique for each set of fibers, detector, and type of lamp.

For each sampling distance r and wavelength λ, the reflectance parameter R'(r, λ) is defined as follows:

$$R'(r, \lambda) = -2.303 \text{ Log (Measured Localized Reflectance)} \quad (9)$$

The absorption coefficient $\mu_a$ and reduced scattering coefficient $\mu_s'$ of the skin tissue were deduced from localized reflectance data by numerical simulation by means of a Monte Carlo method, which, in turn, was calibrated by experimental data for tissue-simulating phantoms.

In addition to calculating the absorption and scattering coefficients, another calculation scheme involved fitting hemoglobin concentration data and hematocrit value data to localized reflectance values [R'(d, λ)] measured at a light collecting element located at a selected distance from the light introduction site ($r_6$ in this example). See TABLE 5.

$$R'(d, \lambda) = -2.303 \text{ Log (Reflectance signal at sampling distance } d\text{)} \quad (10)$$

The use of a selectable detection distance has been described in U.S. application Ser. No. 09/366,084, filed Aug. 3, 1999, incorporated herein by reference.

A classical least square regression (CLSQ) method was used to establish calibration and validation models according to equation (8). The performance of a model was judged by the standard error of calibration (SEC) and the calibration correlation coefficient ($r_c$). The optical parameters selected and the number of the terms in the linear model were selected on the basis of the highest value of $r_c$ and the lowest value of SEC. A four-term model generally provided optimal results. Models employing two or three terms resulted in significantly poorer values of $r_c$ and SEC. When more than four terms were used in the model, the model became unstable, probably due to overfitting.

The ability of a model to predict the concentration of hemoglobin and the value of hematocrit was tested by the so-called leaving-one-out cross validation method, previously described. The standard error of prediction (SEP) and the prediction correlation coefficient $r_p$, based on comparison between the predicted concentration of hemoglobin and the predicted value of hematocrit and the reference concentration of hemoglobin and the reference value of hematocrit, were calculated for different populations and discussed in EXAMPLES 2, 3, and 4.

Example 2

Ten subjects were tested repeatedly (typically three times) over a three week period by means of the apparatus described in EXAMPLE 1. The subjects had both limited ethnic diversity and light skin color. Invasive blood sampling was performed within 15 minutes of the optical measurement. The signal detection module 16 was mounted in a fixture that replaced the armrest of a blood collection chair. Each subject sat in the testing chair with the left forearm placed on an armrest-type human interface module that was mounted on the arm of the chair. In each test, the localized reflectance R(r) data were collected at the six distances shown in TABLE 1 and at three temperature settings, 25° C., 34° C., and 41° C., sequentially. The testing site on the forearm was unchanged for each temperature change. Blood samples were drawn into EDTA tubes while the subject was sitting in the testing chair. The blood samples were drawn immediately before starting or immediately after completing the optical measurement. Reference hemoglobin concentration values were determined by a photometric method that employed a standard clinical instrument, Abbott Vision® Analyzer (Abbott Laboratories, North Chicago, Ill.). Absorption of the heme moiety, released from hemoglobin at pH 12, was determined at wavelengths of 577 nm and 633 nm. The hemoglobin reference method was checked before the measurements by performing control hemoglobin runs. Reproducibility of control runs is reported in the assay manual as 3% CV, or about 0.45 g/dL. Hematocrit values were determined by a standard microcentrifuge method (M. W. Morris, F. R. Davey, "Basic examination of blood", *Clinical Diagnosis and Management by Laboratory Methods*, J. B. Henry, ed., W. B. Saunders Company (Philadelphia, Pa.: 1996), pages 549–559). Both the hemoglobin and hemoatocrit reference determinations were run as single samples with no repeats. The Institutional Review Board had approved the foregoing test protocol for use with human subjects.

Analysis of the data of EXAMPLE 2 involved the conversion of localized reflectance data [R (r, $\lambda$)] into absorption and scattering coefficients. Consequently, $\mu_a$ and $\mu_s'$ were obtained at the six wavelengths of 590 nm, 650 nm, 750 nm, 800 nm, 900 nm, and 950 nm and at the three temperatures of 25° C., 34° C., and 41° C. A calibration model for the non-invasive determination of hemoglobin was obtained by CLSQ regression for the six $\mu_a$ and six $\mu_s'$ values at 34° C. Model No. 1 in TABLES 4 and 5 shows the calibration results in an optimal four-term linear model, in which $\mu_a$ is measured at four wavelengths. Model No. 3 in TABLES 4 and 5 shows the corresponding CLSQ fitting for the hematocrit values for the same subjects using $\mu_a$ and $\mu_s'$ values at 34° C. The optimal correlation was obtained at the same four wavelengths (590 nm, 750 nm, 800 nm, and 950 nm) for both the hemoglobin values, as shown by Model No. 1, and the hematocrit values, as shown by Model No. 3. The calibration correlation coefficient $r_c$ for hemoglobin was 0.83 and the SEC was 0.73 g/dL. The prediction correlation coefficient $r_p$ was 0.69 and the SEP was 0.95 g/dL. The correlation coefficient $r_c$ for hematocrit was 0.78 and the SEC was 2.78%. The prediction correlation coefficient $r_p$ was 0.65 and the SEP was 3.53%. The number of data points for the hematocrit correlation was only 22, because the reference hematocrit values could not obtained for four of the blood samples.

TABLE 4

| Model No. | [Hb] (g/dL) or Hct (%), as a Four-Term Linear Regression Expression |
|---|---|
| 1 | [Hb] (g/dL) = 12.65 + 1.47$\mu_a$ (@ 590 nm) − 25.97$\mu_a$ (@ 750 nm) + 18.93$\mu_a$ (@ 800 nm) + 5.120$\mu_a$ (@ 950 nm) |
| 2 | [Hb] (g/dL) = 11.91 − 12.20$\mu_a$ (@ 750 nm) + 12.85$\mu_a$ (@ 950 nm) − 48.28$\Delta\delta_T$ (@ 750 nm) + 42.42$\Delta\delta_T$ (@ 950 nm) |
| 3 | Hct (%), = 34.56 − 7.96$\mu_a$ (@ 590 nm) − 104.5$\mu_a$ (@ 750 nm) + 81.01$\mu_a$ (@ 800 nm) + 18.10$\mu_a$ (@ 950 nm) |
| 4 | Hct (%), = 67.31 + 22.17$\mu_a$ (@ 650 nm) − 162.0$\mu_a$ (@ 750 nm) + 127.3$\mu_a$ (@ 800 nm) − 235.4$\Delta\delta_T$ (@ 800 nm) |

TABLE 5

| | Model | | Sample Size | | Calibration | | Cross Validation | | |
|---|---|---|---|---|---|---|---|---|---|
| | No. | Parameter | Subjects | Data points | $r_c$ | SEC | $r_p$ | SEP | T (° C.) |
| Hb | 1 | $\mu_a, \mu_s'$ | 10 | 26 | 0.83 | 0.73 g/dL | 0.69 | 0.95 g/dL | 34 |
| Hb | 2 | $\mu_a, \Delta\delta_T$ | 10 | 26 | 0.87 | 0.63 g/dL | 0.82 | 0.75 g/dL | 25, 34, 42 |
| Hct | 3 | $\mu_a, \mu_s'$ | 10 | 22 | 0.78 | 2.78% Hct | 0.65 | 3.53% Hct | 34 |
| Hct | 4 | $\mu_a, \Delta\delta_T$ | 10 | 22 | 0.85 | 2.35% Hct | 0.75 | 2.99% Hct | 25, 34, 42 |

Least square regression of the same data of EXAMPLE 2 was performed using other optical parameters deduced from $\mu_a$ and $\mu_s'$. These parameters included the effective attenuation coefficient $\mu_{eff}$, light penetration depth in tissue $\delta(1/\mu_{eff})$, and change in light penetration depth as a result of temperature change between 25° C. and 41° C. ($\Delta\delta_T$).

Model No. 2 in TABLE 4 gives the CLSQ regression equation for the calibration of in vitro-determined hemoglobin values using $\mu_a$ and $\mu_s'$ values at 34° C., along with the $\Delta\delta_T$ values between 25° C. and 41° C. The correlation coefficients and the standard errors for the non-invasive determination of hemoglobin involving the absorption coefficients at 34° C. and the temperature-dependent optical parameter $\Delta\delta_T$, are given in TABLE 5 for Model No. 2.

The $\Delta\delta_T$ term in Model No. 2 represents the difference in $\delta$ at the two temperatures, the difference being determined at a given wavelength, i.e., $$\Delta\delta_T = \delta(25°\text{ C.}) - \delta(41°\text{ C.}) \tag{11}$$

Thus $\Delta\delta_T$ (@750 nm) is the difference in the light penetration depth resulting from the temperature change between 25° C. and 41° C., determined at a wavelength of 750 nm.

Model No. 4 in TABLE 4 gives the corresponding CLSQ regression equation for the calibration of in vitro-determined hematocrit values of the same subjects using $\mu_a$ and $\mu_s'$ values at 34° C., along with the $\Delta\delta_T$ values between 25° C. and 41° C. The correlation coefficients and the standard errors for the non-invasive determination of hematocrit involving the absorption coefficients at 34° C. and the temperature-dependent optical parameter $\Delta\delta_T$ values between 25° C. and 41° C. are given in TABLE 5 for Model No. 4.

The calculated value of $r_c$ for hemoglobin, using $\mu_a$ at 34° C., increased to 0.87, and the SEC decreased to 0.63 g/dL, when $\Delta\delta_T$ values between 25° C. and 41° C. were included in the regression equation. The calculated value of $r_p$ increased to 0.82, and the SEP decreased to 0.75 g/dL, when $\Delta\delta_T$ values between 25° C. and 41° C. were included in the regression equation. Model No. 2 has absorption terms at wavelengths of 750 nm and 950 nm and $\Delta\delta_T$ terms at the same two wavelengths.

The CLSQ regression equation for hematocrit, Model No. 3 in TABLE 4, has absorption coefficient terms at the wavelengths 590 nm, 750 nm, 800 nm, and 950 nm. For hematocrit, the value of $r_c$ increased from 0.78 to 0.85 when a model containing absorption coefficient terms at the wavelengths 650 nm, 750 nm, and 800 nm at 34° C. was used, along with $\Delta\delta_T$ value between 25° C. and 41° C. at the wavelength 800 nm. The SEC decreased from 2.78% to 2.35% when a model containing absorption coefficient terms at the wavelengths 650 nm, 750 nm, and 800 nm at 34° C. was used, along with $\Delta\delta_T$ value between 25° C. and 41° C. at the wavelength 800 nm. The prediction values also improved, with $r_p$ increasing from 0.65 to 0.75 and SEP decreasing from 3.53% to 2.99%. See Model No. 4, TABLE 4. The number of data points for the hematocrit correlation was only 22, because the reference hematocrit values could not obtained for four of the blood samples.

The temperature limits of 25° C. and 41° C. of this example were used to illustrate the method of this invention. Other temperatures can be selected and used to achieve similar or better results, while maintaining a reasonable comfort level for the patients, without deviating from the spirit of this invention.

It is important to discuss the effect of including $\Delta\delta_T$ in the fitting model. While inclusion of all other deduced optical parameters such as $\mu_{eff}$ and $\delta$ did not improve fitting results, change in penetration depth due to temperature change improved both the correlation coefficient and the standard errors for hemoglobin, as shown by Model No. 2 in TABLES 4 and 5. Inclusion of the change in light penetration depth parameter ($\Delta\delta_T$) in the correlation equation also led to improvement in the values of $r_c$, $r_p$, SEC, and SEP for the non-invasive determination of hematocrit, as compared with models comprising only $\mu_a$ terms, as shown by Model No. 4 in TABLES 4 and 5.

Example 3

In this example, 28 subjects were tested by means of the apparatus described in EXAMPLE 1 at a single temperature, 34° C. The study involved a population with great ethnic diversity, including Caucasian, Oriental, and African-American subjects. Blood samples were drawn into EDTA tubes while the subject was sitting in the testing chair. The blood samples were drawn immediately before starting or immediately after completing the optical measurement. Reference hemoglobin concentration and hematocrit values were determined in the manner described in EXAMPLE 2. Four subjects had dark skin color. Silicone oil (poly-(dimethylsiloxane) 200®fluid, Aldrich Chemical Company, Cat. No. 37,839-9) was applied to the interface between the skin and the temperature-controlled optical probe. The Institutional Review Board had approved the test protocol for human subjects.

Figure 3A:
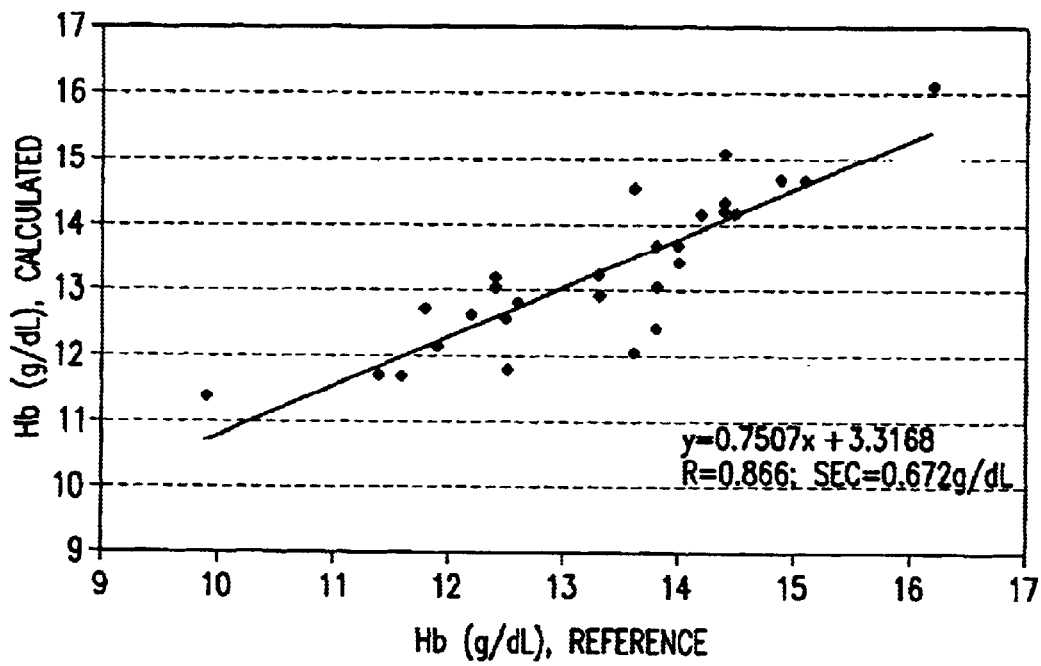
FIG. 3A is an illustration showing a classical least squares (CLSQ) fitting of the hemoglobin (Hb) data for 28 subjects in the experiments of EXAMPLE 3. The points on the graph in the figure represent calculated hemoglobin concentrations of Model No. 5 of EXAMPLE 3.
Figure 3B:
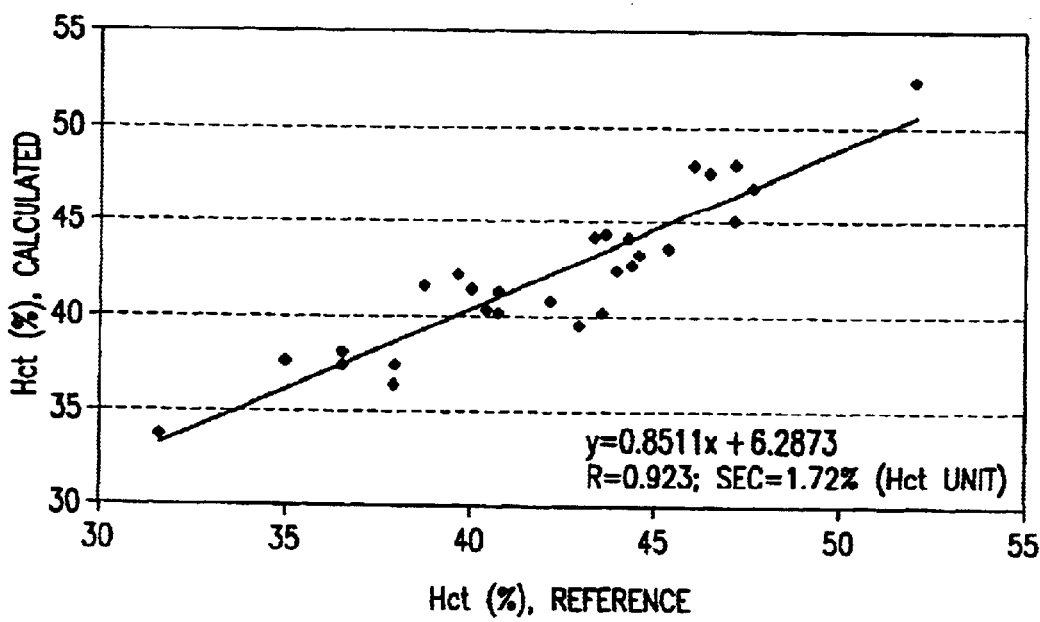
FIG. 3B is an illustration showing a classical least squares (CLSQ) fitting of the hematocrit (Hct) data for 28 subjects in the experiments of EXAMPLE 3. The points on the graph in the figure represent calculated hemoglobin concentrations of Model No. 7 of EXAMPLE 3.

The data were analyzed in two different ways. First, the data was analyzed as reflectance parameters at the six distances shown in TABLE 1 and at the six wavelengths of 590 nm, 650 nm, 750 nm, 800 nm, 900 nm, and 950 nm [R'(r, $\lambda$)]. For hemoglobin, Model No. 5 in TABLES 6 and 7 was obtained by searching through all possible four-term linear combinations based on R'(r, $\lambda$) at six sampling distances and six wavelengths for all of the 28 subjects. Model No. 7 in TABLES 6 and 7 shows the result of CLSQ regression analysis of hematocrit for the 28 subjects who participated in this study. This model used all spatially resolved diffuse reflectance values, R'(r, $\lambda$), at all sampling distances and wavelengths. The predicted correlation coefficient for hemoglobin, $r_p$, was 0.80, and the SEP was 0.81 g/dL. These values were close to those obtained by including the temperature dependence of penetration depth in the fitting equation (Model No. 2). For hematocrit, the predicted correlation coefficient, $r_p$, was 0.89, and the SEP was 2.05%. FIG. 3 shows the results of CLSQ fitting of the hemoglobin and hematocrit data for the 28 subjects from this study when all reflectance values [R'(r, $\lambda$)] at the six distances and six wavelengths were used in the CLSQ regression analysis. The hematocrit data compared well with the data reported by Zhang, et al. for 10 Caucasian subjects undergoing cardiac bypass surgery. Zhang, et al. disclose the use of the region of the spectrum ranging from 581 nm to 1000 nm for detection and the use of partial least squares regression for data analysis. The optimal model of Zhang et al. required eight factors, and the reported prediction correlation coefficient, $r_p$, was 0.77, and the SEP was 2.16%. See Zhang et al., "Investigation of noninvasive in vivo blood hematocrit measurement using NIR reflectance spectroscopy and partial least squares regression" Applied Spectroscopy, volume 54, pages 294–299 (2000).

A second method for the analysis of the data in this study involved the use of reflectance values at a single sampling distance and at a plurality of wavelengths [R'(d, $\lambda$)]. Model No. 6 in TABLES 6 and 7 was obtained by searching through all possible four-term linear combinations, for the hemoglobin values in 28 subjects, based on reflectance signals at a light collection site at a unique ampling distance. The sampling distance between the light collection site and the light introduction site was 1.84 mm, which is equal to $r_6$.

The R'(d, λ) data analysis for the hematocrit value is given by Model No. 8. The data from most distant light collection site (a sampling distance of 1.84 mm) resulted in the highest correlation coefficient and lowest SEC, as shown by Model No. 8 in TABLES 6 and 7. Model No. 8 in TABLES 6 and 7 also shows the hematocrit fitting results for the 28 subjects who participated in the study, using reflectance values at a single sampling distance and a plurality of wavelengths.

TABLE 6

| Model No. | [Hb] (g/dL) or Hct % as a Four-term Linear Regression Expression |
|---|---|
| 5 | [Hb] g/dL = −3.68 + 8.84R' ($r_4$, @590 nm) − 12.06R' ($r_5$, @650 nm) − 61.48R' ($r_6$, @900 nm) + 67.74R' ($r_6$, @950 nm) |
| 6 | [Hb] g/dL = −2.79 + 5.93R' (@590 nm) − 8.02R' (@650 nm) − 62.36R' (@900 nm) + 67.13R' (@950 nm) |
| 7 | Hct % = 44.00 + 35.04R' ($r_2$, @590 nm) − 37.23R' ($r_3$, @750 nm) − 148.5R' ($r_6$, @800 nm) + 147.5R' ($r_6$, @950 nm) |
| 8 | Hct % = −0.3473 + 39.03R' (@590 nm) − 60.96R' (@650 nm) − 151.3R' (@900 nm) + 177.9R' (@950 nm) |

TABLE 7

| | Model | | Sample Size | | Calibration | | Cross Validation | |
|---|---|---|---|---|---|---|---|---|
| | No. | Parameter | Subjects | Data points | $r_c$ | SEC | $r_p$ | SEP |
| Hb | 5 | R' (r, λ) | 28 | 28 | 0.87 | 0.67 g/dL | 0.80 | 0.81 g/dL |
| Hb | 6 | R' ($r_6$, λ) | 28 | 28 | 0.83 | 0.75 g/dL | 0.74 | 0.91 g/dL |
| Hct | 7 | R' (r, λ) | 28 | 28 | 0.92 | 1.72% Hct | 0.89 | 2.05% Hct |
| Hct | 8 | R' ($r_6$, λ) | 28 | 28 | 0.91 | 1.84% Hct | 0.85 | 2.42% Hct |

Example 4

The ability of the non-invasive method of this invention to screen blood donor eligibility was tested in parallel with invasive test methods. Prospective donors for a blood drive were asked to volunteer for the non-invasive test procedure before they went to a blood donation center. The blood drive was conducted by a local blood bank; -blood donation and the non-invasive test were not related activities. A total of 19 prospective blood donors volunteered for the non-invasive test. Volunteers were asked to report whether they were accepted for donation or rejected based on their hemoglobin value. At the donation center, blood bank personnel determined blood hemoglobin (iron) level by means of a finger stick sample. To be eligible for donation, the minimum requirement for hemoglobin concentration in a prospective donor was 12.5 g/dL. The non-invasive test was performed in the same manner as described in EXAMPLE 3 with the temperature of the skin maintained at 34° C. (i.e., approximately 3° C. below the body core temperature).

Figure 4:
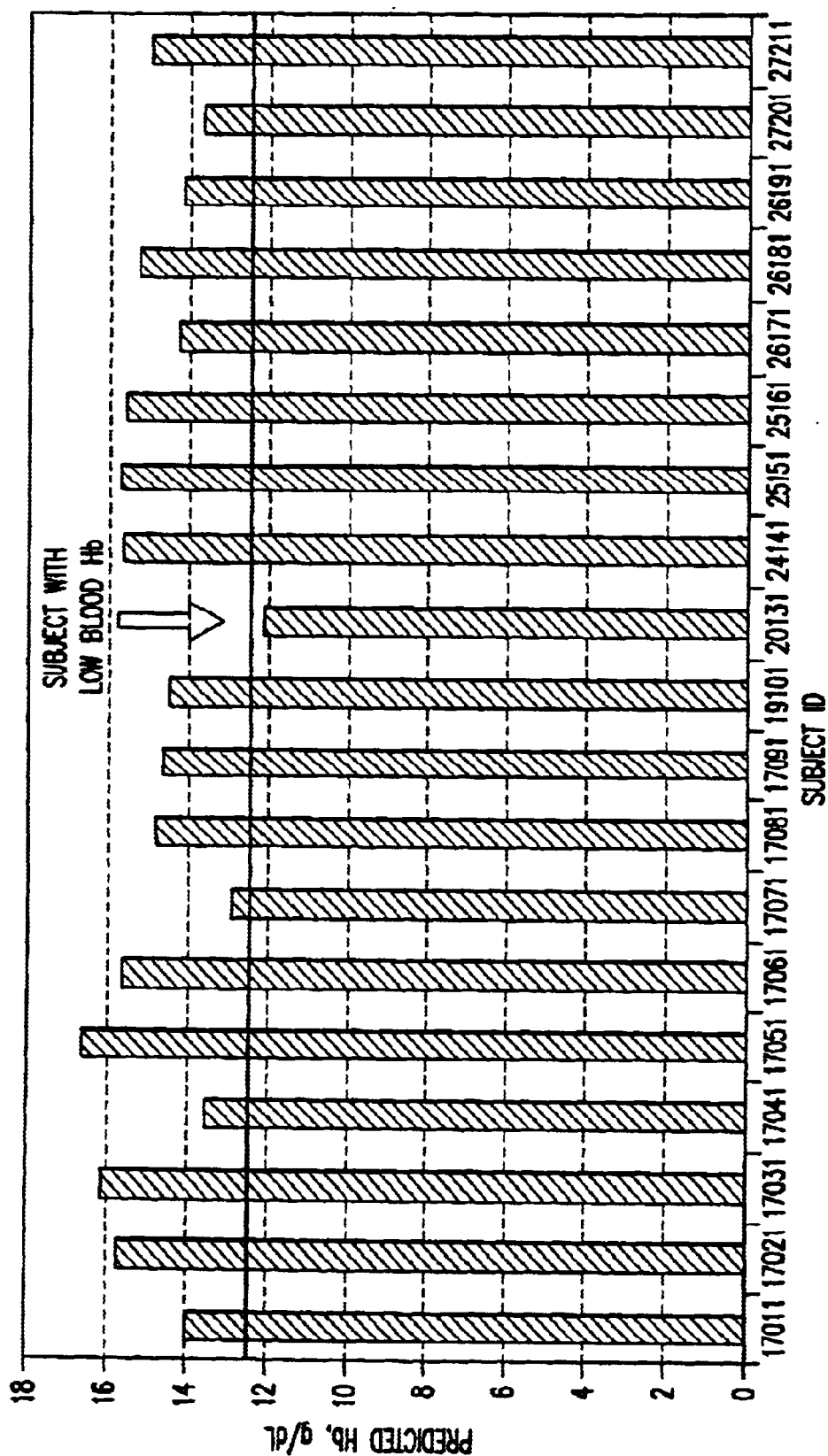
FIG. 4 is an illustration showing calculated hemoglobin (Hb) values for 19 prospective voluntary blood donors. The values were calculated by means of an algorithm deduced from Model No. 5 of EXAMPLE 3. The numbers on the X-axis are arbitrary identification numbers assigned to the subjects.

The spatially resolved diffuse reflectance data was collected for each prospective donor at the six wavelengths 590 nm, 650 nm, 750 nm, 800 nm, 900 nm, and 950 nm and at the six sampling distances shown in TABLE 1. The temperature of the TCLRTP probe was maintained at 34° C. The R'(r, λ) data was used to predict the concentration of hemoglobin for each donor using Model No. 5 of EXAMPLE 3 and the previous data set for the 28 volunteers as the calibration set. The hemoglobin concentration was then predicted using CLSQ regression of the optical data and the stored calibration set. The result of the donor screening experiment is shown in FIG. 4. The hemoglobin values on the Y-axis were calculated by means of an algorithm deduced from Model No. 5. The numbers on the X-axis are arbitrary identification numbers assigned to the subjects. Out of the 19 prospective donors, only one donor was rejected by the blood bank as having a low hemoglobin value (less than 12.5 g/dL). The same donor was identified as anemic by analysis of the R(r, λ) data at 34° C. Thus, it was possible to use the detection method of this invention and the appropriate algorithm to predict and screen anemic donors prior to blood donation, thus alleviating the need for invasive testing and use of finger-stick blood sampling prior to donation. The same method can also be used for the determination of hemoglobin concentration in infants and lactating mothers or pregnant women, without the pain associated with invasive blood sampling.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for the non-invasive determination of hemoglobin concentration and hematocrit value in human tissue, said method comprising the steps of:

(a) setting the temperature of an area of skin of a body part to a first temperature, said first temperature being below the core temperature of the body, (b) performing an optical measurement in which at least one light introduction site on the surface of said skin is illuminated by a light beam at a plurality of wavelengths and the light re-emitted from the underlying dermal layers is collected at at least one light collection site, the at least one light introduction site and the at least one light collection site being separated by at least one sampling distance, the at least one sampling distance between said at least one light introduction site and said at least one collection site being selected to restrict the sampling depth of said body part to within the epidermis layer and dermis layer only, whereby contributions from light re-emitted from adipose tissue and muscle tissue are minimized and contributions from light re-emitted from the epidermis and dermis layers are collected, said temperature being maintained at a constant value during said optical measurement, (c) setting the temperature of said area of said skin of said body part to at least a second temperature that is within the physiological temperature range, (d) repeating step (b) at said at least second temperature, (e) determining a plurality of optical parameters at each temperature and determining the dependence of at least one of said aforementioned optical parameters on temperature, (f) establishing a calibration relationship that relates (1) at least one of said plurality of optical parameters at a given temperature and (2) the dependence of at least one of said plurality of optical parameters on temperature with the concentration of hemoglobin or the hematocrit value measured independently, and (g) determining the concentration of hemoglobin or the hematocrit value by means of a subsequent determination of the plurality of optical parameters at a given temperature and the dependence of the at least one of said aforementioned optical parameters on temperature and the calibration relationship established in step (f), wherein said biological sample comprises intake human tissue.

2. The method of claim 1, wherein said temperatures at which said area of said skin is maintained ranges from about 15° C. to about 42° C.

3. The method of claim 1, wherein said temperatures at which said area of said skin is maintained ranges from about 20° C. to about 40° C.

4. The method of claim 1, wherein said at least one wavelength of light used ranges from 400 nm to 2500 nm.

5. The method of claim 1, wherein said at least one optical parameter is selected from the group consisting of absorption coefficient, scattering coefficient, effective attenuation coefficient, and light penetration depth in tissue.

6. The method of claim 1, wherein said dependence of optical parameters on temperature includes change in the light penetration depth in tissue as a function of temperature.

7. The method of claim 1, wherein said optical measurement is a spatially resolved diffuse reflectance measurement.

8. The method of claim 1, wherein said distance between said at least one light introduction site and said at least one light collection site ranges from about 0.1 mm to about 10 mm.

9. The method of claim 1, wherein said area of skin of said body part under temperature control and being optically examined covers a volume of tissue ranging from about 0.1 to about 10 cubic millimeters.

10. The method of claim 1, wherein said volume of tissue under temperature control and being optically examined ranges from about 0.2 to about 5 cubic millimeters.

11. The method of claim 1, wherein said volume of tissue under temperature control and being optically examined ranges from about 0.2 to about 2 cubic millimeters.

12. The method of claim 1, wherein said method for establishing said calibration relationship is selected from the group consisting of linear least squares, partial least squares, and principal component analysis.

13. A method for the determination of hemoglobin and hematocrit in human body, said method comprising the steps of:

(a) setting the temperature of an area of skin of a body part to a given temperature, the given temperature being below the core temperature of the body, (b) performing an optical measurement in which at least one light introduction site on the surface of the skin is illuminated by a light beam at a plurality of wavelengths and the light re-emitted from the underlying dermal layers is collected at at least one light collection site, the at least one light introduction site and the at least one collection site being separated by at least one sampling distance, the at least one sampling distance between the at least one light introduction site and the at least one light collection site being selected to restrict the sampling depth of the body part to within the epidermis layer and dermis layer only, whereby contributions from light re-emitted from adipose tissue and muscle tissue are minimized and contributions from light re-emitted from the epidermis and dermis ayers are collected, the given temperature being maintained at a constant value during the optical measurement, whereby the optical measurement generates a measurable signal corresponding to at least one optical parameter, (c) correlating the measurable signal of step (b) with hemoglobin concentration or hematocrit value determined by an independent method to establish a calibration relationship, and (d) determining the concentration of hemoglobin or the hematocrit value from a signal from a subsequent optical measurement and the calibration relationship of step (c), wherein said biological sample comprises intact human tissue.

14. The method of claim 13, wherein said temperatures at which said area of said skin is maintained ranges from about 15° C. to about 42° C.

15. The method of claim 13, wherein said temperatures at which said area of said skin is maintained ranges from about 20° C. to about 40° C.

16. The method of claim 13, wherein said at least one wavelength of light used ranges from 400 nm to 2500 nm.

17. The method of claim 13, wherein said at least one optical parameter is selected from the group consisting of absorption coefficient, scattering coefficient, effective attenuation coefficient, and light penetration depth in tissue.

18. The method of claim 13, wherein said optical measurement is a spatially resolved diffuse reflectance measurement.

19. The method of claim 13, wherein said distance between said at least one light introduction site and said at least one light collection site ranges from about 0.1 mm to about 10 mm.

20. The method of claim 13, wherein said area of skin of said body part under temperature control and being optically examined covers a volume of tissue ranging from about 0.1 to about 10 cubic millimeters.

21. The method of claim 13, wherein said area of skin of said body part under temperature control and being optically examined covers a volume of tissue ranging from about 0.2 to about 5 cubic millimeters.

22. The method of claim 13, wherein said area of skin of said body part under temperature control and being optically examined covers a volume of tissue ranging from about 0.2 to about 2 cubic millimeters.

23. The method of claim 13, wherein said method for establishing said calibration relationship is selected from the group consisting of linear least squares, partial least squares, and principal component analysis.

\* \* \* \* \*

UNITED STATES PATENT AND TRADEMARK OFFICE
CERTIFICATE OF CORRECTION

PATENT NO. : 6,662,031 B1
DATED : December 9, 2003
INVENTOR(S) : Omar S. Khalil et al.

It is certified that error appears in the above-identified patent and that said Letters Patent is hereby corrected as shown below:

<u>Column 24,</u>
Line 10, replace "avers" with -- layers --.

Signed and Sealed this

Thirty-first Day of January, 2006

JON W. DUDAS
*Director of the United States Patent and Trademark Office*